United States Patent [19]

Begley

[11] Patent Number: 4,766,551
[45] Date of Patent: Aug. 23, 1988

[54] METHOD OF COMPARING SPECTRA TO IDENTIFY SIMILAR MATERIALS

[75] Inventor: Timothy H. Begley, Cheverly, Md.

[73] Assignee: Pacific Scientific Company, Anaheim, Calif.

[21] Appl. No.: 909,952

[22] Filed: Sep. 22, 1986

[51] Int. Cl.[4] .............................................. G06F 7/04
[52] U.S. Cl. .................................. 364/498; 250/307; 356/388; 356/448
[58] Field of Search ............... 364/498, 525, 526, 507; 356/326, 388–390, 445, 446, 448; 250/306–308, 334, 340–342

[56] References Cited

U.S. PATENT DOCUMENTS

| | | | |
|---|---|---|---|
| 4,590,574 | 5/1986 | Edmonds et al. | 364/498 |
| 4,660,151 | 4/1987 | Chipman et al. | 364/498 |

OTHER PUBLICATIONS

Reid et al., *Applied Spectroscopy*, vol. 20, No. 5, 1966, pp. 320–325, "Data-Reduction and Search System for Digital Absorbance Spectra".
Tanabe et al., *Analytical Chemistry*, vol. 47, No. 1, Jan. 1975, pp. 118–122, "Computer Retrieval of Infrared Spectra by a Correlation Coefficient Method".
de Haseth, *Analytical Chemistry*, vol. 53, No. 14, pp. 2292–2298, "Interferogram-Based Infrared Search System".

*Primary Examiner*—Parshotam S. Lall
*Assistant Examiner*—Brian M. Mattson
*Attorney, Agent, or Firm*—Lane and Aitken

[57] ABSTRACT

In a method of identifying or comparing compositions of material, the reflectivity of a material to be identified or compared is measured at index points distributed through the near infrared spectrum. A similar measurement is made for at least one standard or known material. From the reflectivity measurements, sets of values representing the first or higher order derivative curves are determined. These values mathematically define vectors by representing the coordinates of the end points of the vectors and multiple dimensional space. An index of a similarity between the composition of a test sample and a standard material is calculated by determining the cosine of the angle between the corresponding vectors.

10 Claims, 3 Drawing Sheets

METHOD OF COMPARING SPECTRA TO IDENTIFY SIMILAR MATERIALS

FIELD OF THE INVENTION

The present invention relates to analytic methods and apparatus for identifying materials and their compositions, more particularly, for identifying similar materials and thereby assuring the purity of chemical products.

BACKGROUND OF THE INVENTION

One way of identifying or comparing compositions of materials is by comparing graphs showing the reflectivity of the materials to energy in a given part of the electromagnetic spectrum. Visual or numerical comparison is made of the spectral width and placement of peaks within the given portion of the spectrum. Both the mid-infrared and near-infrared ranges are commonly used, but each of those ranges is problematic. In the near-infrared range, peaks for different materials are not as easily distinguished as in the remainder of the infrared range, a lack of resolution that introduces interpretive errors into the measurements. However, in the mid-infrared range measurements are more prone to include artifacts, errors that are introduced during the preparation of the sample which must be measured in a thin layer and under carefully standardized conditions. In particular, measurements in the mid-infrared range are highly sensitive to common sample handling problems and subtle variations in the physical condition of the sample.

SUMMARY OF THE INVENTION

The method and apparatus in accordance with the present invention is particularly well adapted to provide a more reliable indication of similarlity between compositions of material by more clearly indicating the degree of similarity or difference in their reflectivity characteristics in a near infrared range of the spectrum. This result is achieved using relatively modest computing capacity.

In accordance with the method of the present invention, reflectivity values and for the sample and for the standard, respectively, are measured at incrementally spaced index points distributed through the near-infrared spectrum. The resulting sets of values obtained by the measurements represent curves corresponding to the variation in the reflectivity of the sample and the standard respectively with wavelength in the near infrared spectrum. From the reflectivity measurements, sets of values representing the first or higher order derivative curves are determined. The values of the sets representing the derivative curves define vectors by representing the coordinates of the end points of the vectors in multidimensional space with the number of dimensions equaling the number of values in the set. An index of the similarity of the composition of the sample and standard materials is then calculated by determining the cosine of the angle between the two vectors. This method provides a reliable indication of the similarity of dissimilarity of the composition of the sample and the standard and accordingly a measurement of acceptability of the sample and the batch from which it is taken.

In an alternative embodiment the composition of an unknown material is identified by defining a vector for the unknown material as described above and determining the cosine of the angle between the vector and vector similarly defined for a multiplicity of known materials, one of which is the same composition as the unknown material. The highest cosine value determined will identify the composition of the unknown material as the same as that corresponding to the highest cosine value.

In the method of invention, it is important for sets of values to be determined from the reflectivity data to represent the first or higher order derivative curves from the measured reflectivity data. The reflectivity data could be compared without taking the derivative making use of the vector method of comparison described above, wherein each set of reflectivity data would represent the coordinates of the end points of a vector and the cosine of the angle between the materials. However, when such a comparison is made on reflectivity data without first computing the derivative, the cosine determined between vectors for materials of different compositions in many instances is not markedly different from the cosine determined between the vectors for materials which are of the same composition. The present invention, by determining sets of values representing derivatives of the curves represented by the reflectivity data and using these latter sets of values to represent vectors between which the cosine of the angle is determined, provides a measurement which varies sharply when the composition of the materials are the same and when they are different even to only a minor degree. When the compositions are the same, the cosine is close to unity and when the compositions are not the same, the cosine is not near unity. Thus, the present invention provides a highly reliable method of identifying material.

BRIEF DESCRIPTION OF THE DRAWINGS

The features and advantages of the present invention will be more clearly understood when the detailed description of a preferred embodiment described below is considered in conjunction with the drawing provided in which.

DESCRIPTION OF THE PREFERRED EMBODIMENTS

The present invention makes use of a known technique of comparing two sets of values, such as the values representing the amplitude of a curve at incrementally spaced points along the curve, by assuming that each set of values represents a vector wherein each value of the set represents a different coordinate of the end point of a vector in multidimensional space. Thus, if there are n values in the set, then the vector represented by this set will be a vector in n-dimensional space. An index of the similarity between two sets of values, and accordingly an index of the similarity of the two curves represented by the two sets of values, can be determined by determining the cosine of the angle between the two vectors represented by the two sets of values. The cosine of the angle between the two sets of values is determined by computing the dot product of the two vectors and dividing the dot product by the product of the amplitude of the two vectors. This computation is represented symbolically as follows:

$$\text{Cosine}\theta = \frac{A \cdot B}{|A| \, |B|}$$

in which $\theta$ is the angle between the two vectors A and B, A·B is the dot product between the two vectors, $|A|$ is the amplitude of the vector A and $|B|$ is the amplitude of the vector B. To compute the dot product A·B of the vectors A and B, the sum of the products of the corresponding coordinates is determined. Thus, $$A \cdot B = \sum_{i=1}^{n} A_i B_i$$

in which $A_i$ are the values of the coordinates of the vector A and $B_i$ are the values of the coordinates of the vector B. The amplitudes of the vectors A and B are determined as follows:

$$|A| = \left( \sum_{i=1}^{n} A_i^2 \right)^{\frac{1}{2}}$$

$$|B| = \left( \sum_{i=1}^{n} B_i^2 \right)^{\frac{1}{2}}$$

Thus the cosine of the angle between the two vectors is represented as follows:

$$\text{Cosine}\theta = \frac{\sum_{i=1}^{n} A_i B_i}{\left( \sum_{i=1}^{n} A_i^2 \right)^{\frac{1}{2}} \left( \sum_{i=1}^{n} B_i^2 \right)^{\frac{1}{2}}}$$

Figure 1:
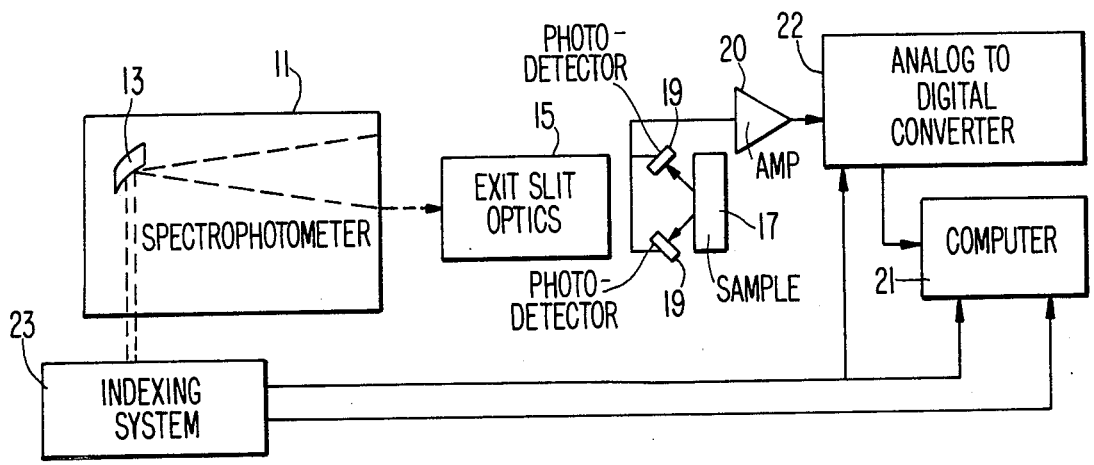
FIG. 1 is a schematic drawing of apparatus for determining an index of similarity in accordance with the present invention.

In accordance with the invention, a series of reflection measurements are carried out by an instrument as shown in FIG. 1. In the instrument the measurements are provided to a computer 21 by a near infrared spectrophotometer 11 comprising oscillating diffraction grating 13. The spectrophotometer directs light with a narrow wavelength band through exit slit optics 15 to a sample 17. As the grating oscillates, the center wavelength of the light that irradiates the sample is swept through the near infra-red spectrum. Light from the defraction grating that is reflected by the sample 17 is detected by infrared photodetectors 19. The photodetectors 19 generate a signal that is transmitted to an analog to digital converter 22 by an amplifier 20. An indexing system 23 generates pulses as the grating 13 oscillates and applies these pulses to the computer 21 and to the analog to digital converter 22. In response to the pulses from the indexing sytem 23, the analog to digital converter 22 converts successive samples of the output signal of the amplifier 20 to digital values, which are stored in the computer 21. Each digital value will thus correspond to the reflectivity of the sample at a specific wavelength in the near infrared. The computer 21 monitors the angular position of the grating 13, and accordingly the wavelength irradiating the sample, as the grating oscillates by counting the pulses produced by the indexing system 23. The pulses produced by the indexing 23 define incremental index points at which values of the output signal of the amplifier 20 are converted to digital values and stored in the computer 21. The index points are distributed incrementally throughout the near infrared spectrum each corresponding to a different wavelength at which the sample is irradiated. The structure and operation of a suitable spectrophotometer is described in greater detail in U.S. Pat. No. 4,264,205.

Figure 2:
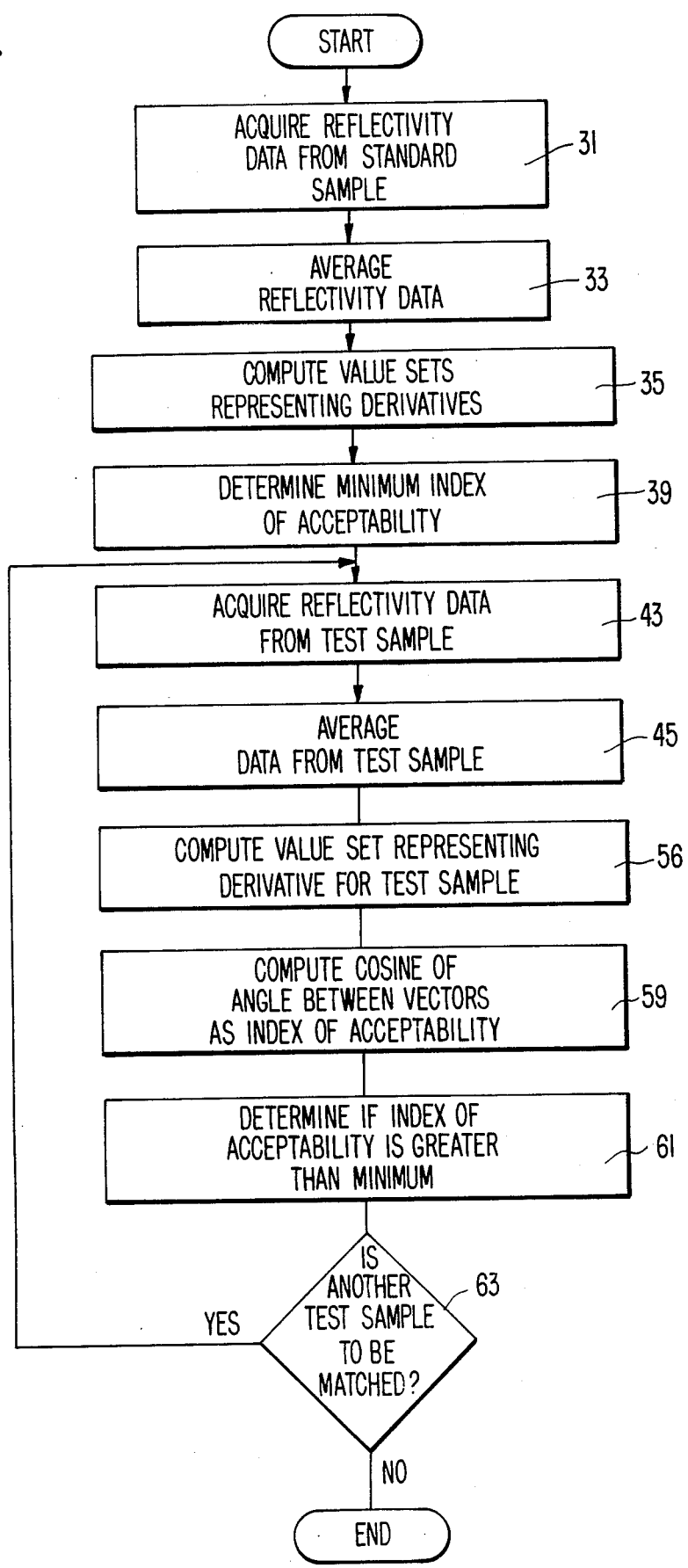
FIG. 2 is a flowchart of a first method in accordance with the present invention.

The process of the invention illustrated in FIG. 2 is designed to determine whether the composition of a test sample is the same as that of the standard sample. In the process, the computer 21 is programmed to receive and store the reflectivity data from a standard sample in instruction sequence 31. In the preferred embodiment the reflectivity is measured five times so that there are 5 sets of reflectivity data obtained from the sample. From these five sets of data, an average reflectivity value is computed for each of the incremental index points along the spectrum in instruction sequence 33. In the specific instrument used in the invention, there are 700 incremental index points so there are 700 values in each set of data obtained by the instrument.

In instruction routine 35, the program computes a set of values from each of the five sets of data representing a derivative of the curve represented by such set of values and also from the set of average values obtained by averaging the five sets of data at each incremental index point. The derivative computed may be the first order derivative or a higher order derivative. The order of the derivative computed will be the same for each set of data. The first order derivative is computed by subtracting each of the values of the set from the value of the set at the next incremental index point. For example, the first order derivative value for the index point k is determined by subtracting the reflectivity measurement value at the index point k-1 from the reflectivity measurement value at the index point k. Higher order differentials are computed in a similar manner from the set of values representing the preceeding lower order derivative. Following instruction sequence 35 there will be six sets of data determined from the standard sample. Five of these sets will represent the derivatives of the curves of the original five reflectivity measurements of the standard. These five sets are designated $S(a)_1$ through $S(a)_n$, $S(b)_1$ through $S(b)_n$, $S(c)_1$ through $S(c)_n$, $S(d)_1$ through $S(d)_n$, and $S(e)_1$ through $S(e)_n$. The remaining value set will represent the derivative of the curve represented by set of average values determined in routine 35. This latter set representing the average value derivative is designated $S_1$ through $S_n$. Since there are 700 values in each set, n will be 700. In instruction sequence 39, each set of values computed in instruction routine 35 is assumed mathematically to represent or define a vector in n-dimensional space, in the manner explained above. The set of values $S(a)_1$ through $S(a)_n$ represent the vector designated $S(a)$. The set of values designated $S(b)_1$ through $S(b)_n$ representing the vector $S(b)$, the set of values $S(c)_1$ through $S(c)_n$ represent the vector $S(c)$, the set of values $S(d)_1$, through $S(d)_n$ represent the vector $S(d)$ and the set of values $S(e)_1$ through $S(e)_n$ represent the vector $S(e)$. Likewise the set of values $S_1$ through $S_n$ represent the vector S. In routine 39 the cosine of the angle between the vector S and each of the vector $S(a)$, $S(b)$, $S(c)$, $S(d)$ and $S(e)$ is computed. A minimum index of acceptability $I_s$ for the samples to be tested is computed from the range of cosine values determined in routine 39 in accordance with the equation $I_s = A - \chi\sigma$ in which:

A is the average of the cosine values determined in routine 39.

$\sigma$ is the variance of the cosine values determined in routine 39.

$\chi$ is an operator specified range value.

Typically the average A might be 0.998, $\sigma$ might be 0.0001, and $\chi$ might be 10 making $I_s = 0.998 - 10(0.0001) = 0.997$. The value of $I_s$ is stored and is also displayed at this time to the operator on the display screen of the computer.

The program then enters into instructions routine 43 at which time a sample from a batch to be tested for acceptability has its reflectivity measured by the instrument of FIG. 1 throughout the infrared spectrum. The test sample is measured five times to obtain five sets of values and these five sets of values are received and stored in the computer in instruction routine 43. The program then enters instruction routine 45 in which the five sets of values acquired in routine 43 are averaged at each index point to obtain a set of average values for the test sample. Following instruction sequence 45, the program, in instruction routine 56, computes the derivative of the curve represented by the averaged set of n values determined in routine 45. The order of the derivative computed must be the same as the order of the derivatives computed in instruction routine 35. The set of n values representing the derivative computed in routine 56 are designated $X_1$ through $X_n$. In instruction routine 59, the set of values $X_1$ through $X_n$ are assumed to represent or define a vector X in n-dimensional space wherein the values of $X_1$ through $X_n$ are the coordinates of the end point of the vector X as explained above. In the routine 59, the program computes the cosine of the angle between the vector X and the vector S in the manner described above. This cosine represents the index $I_x$ of the similarity of the test sample and the standard. If the composition of the materials of the test sample and the standard are essentially the same, this index, or cosine between the two vectors should exceed 0.995 and should be equal to or greater than the value of $I_s$ computed in instruction sequence 39 as the minimum index of similarity.

Following instruction sequence 59, the program enters instruction sequence 61 in which the magnitude of the index value $I_x$ is displayed and is compared with the minimum index value $I_s$ determined in routine 39. If the value of $I_x$ is less than the value $I_s$, the computer displays on the screen the legend "OUT OF TOLERANCE" indicating to the operator that the test sample, and accordingly the batch from which the test sample was obtained, is not of the same composition as that of the standard sample. Any batch found to be out of tolerance in this manner is segregated from the batches in which the index of acceptability $I_x$ is determined to be not less than $I_s$. For example, if the batch is being tested is a product being prepared for shipment, the batch determined to be out of tolerance would be discarded, returned for reprocessing, or shipped as lower quality product. Following decision sequence 61, the program enters decision sequence 63 wherein the operator is asked on the computer screen whether he wants to measure another test sample. If the operator signals "YES", the program returns to instruction sequence 41 and in the process is repeated for the new test sample. If the operator indicates that he is not going to proceed with the testing of another sample the program ends.

The computer program for carrying out the process of FIG. 2 is listed in Fortran in the appendix to this application. (Appendix not included. See application file.)

It is not necessary to perform the instruction sequences and routines 31, 33, 35, and 39 each time the operator wants to test a set of samples. The set of values from a standard sample $S_1$ through $S_n$ and the minimum index value $I_s$ could be previously computed and stored in the computer or on a mass storage device prior to measuring the test samples and the program begins with routine 43 to aquire the reflectivity data from the test sample.

Figure 3:
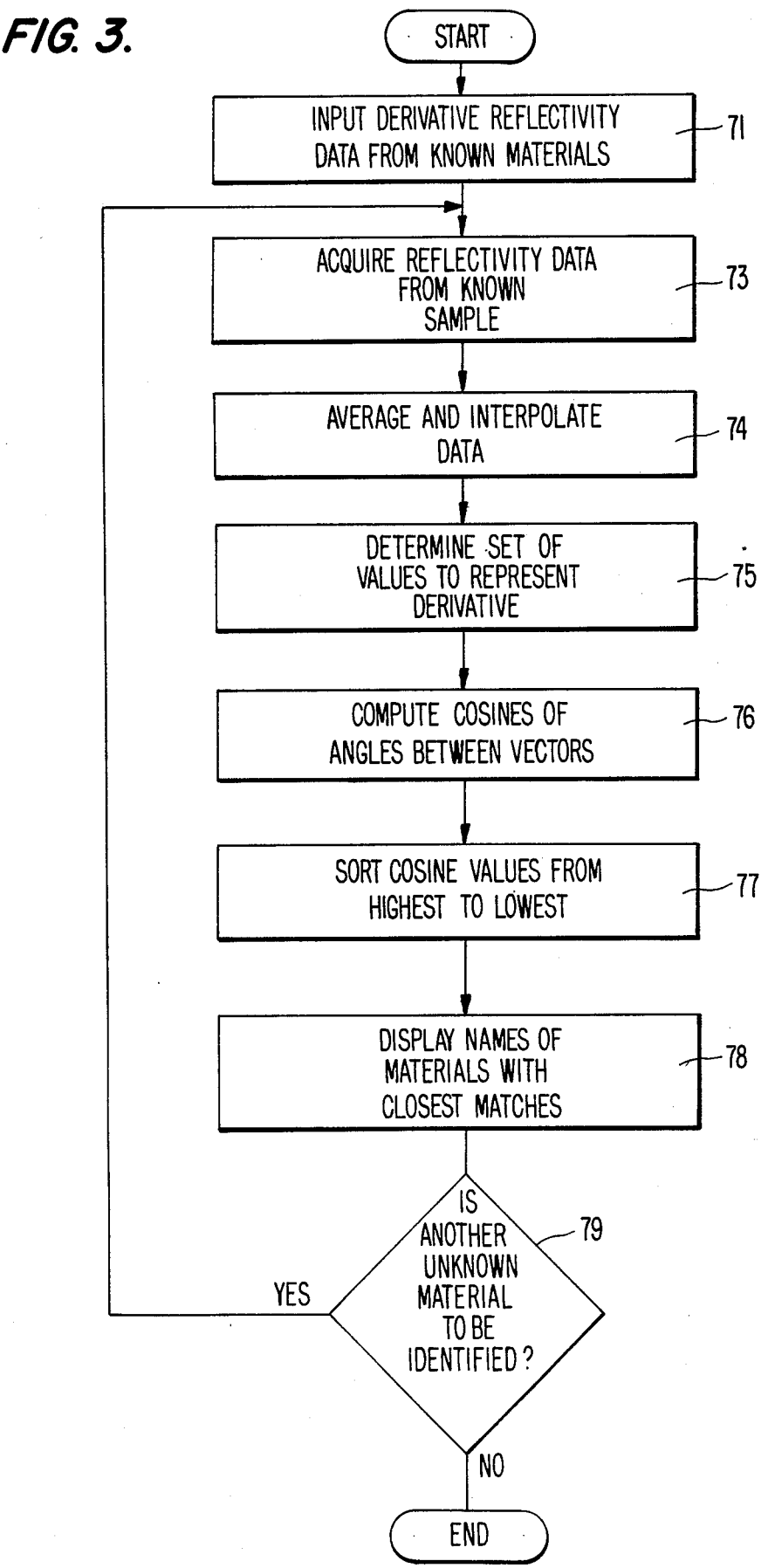
FIG. 3 is a flowchart of a second method in accordance with the present invention.

In the alternative embodiment of the invention shown in FIG. 3, the method of the invention is employed to identify the composition of the material of an unknown sample. In accordance with this embodiment, in instruction sequence 71, the reflectivity data in the near infrared spectrum from a large number of different known materials to be matched to the unknown sample are inputted to the computer. Preferably the unknown material will have the same composition as one of the known materials. The reflectivity data for each different material is a set of values representing a derivative curve for the material computed in the same manner as the derivative curves were computed in the method described with reference to FIG. 2, that is the reflectivity at incrementally spaced index points along the near infrared spectrum is measured by the spectrophotometer and the measurement is repeated five times. The sets of values thus obtained are averaged and from the averaged data, the derivative is computed to provide a set of values for a given material. These sets of values representing the derivative for each known material to be matched with the unknown material are inputted to the computer in instruction sequence 71.

Following instruction sequence 71, the program enters instruction sequence 73 in which the reflectivity data is acquired from the unknown sample. This data represents reflectivity read from the unknown sample by the spectrophotometer in the same manner as described with reference to FIG. 2. Following instruction sequence 73, the program enters routine 74, in which the reflectivity is averaged in the same manner as described above with reference to FIG. 2. Following instruction sequence 74, the program enters routine 75, in which a set of values representing a derivative of the curve represented by the set of values computed in instruction sequence 74 is determined. The order of the derivative determined must be the same as the derivatives represented by the data inputted in instruction sequence 71. The program in the routines 73, 74, and 75 is identical to the program in the process of FIG. 2 in the routines 43, 45, and 56. Following routine 75, in routine 76, the set of values representing the derivative determined in routine 75 is assumed to represent or define a vector in the manner described above. In addition, the reflectivity data inputted in instruction sequence 71 for each material is also assumed to represent or define a vector in the same manner, and the cosine of the angle between the vector represented by the set of values computed in routine 75 and each of the vectors represented by the sets of values inputted in instruction 71 is computed. Then in instruction sequence 77, the cosine values computed in routine 76 are sorted from highest to lowest. If the composition of the material of the unknown sample matches the composition of one of the sets of reflectance data inputted to the computer in instruction sequence 71, then the highest cosine value will be the one computed between the vector for the data of that material and the vector for the unknown sample. This cosine value will be very close to unity.

In instruction sequence 78, the names of a plurality of materials making the closest match by cosine value, along with the computed cosine value for each material is displayed to the operator. From this display, the operator can determine whether the composition of the unknown material matches one of the materials for which data was inputted in instruction sequence 71 and if a match occurs, identify the composition of the unknown material. In addition, the names of other materials which match most closely with the unknown material are displayed.

If none of the cosine values displayed in instruction sequence 78 is close to unity, then the operator knows that the unknown sample material does not match any of the materials for which data was inputted to the computer in instruction sequence 71. From the names of the materials that are displayed as matching most closely to the unknown material, the operator will be given some information from which he may be able to make an educated guess as to the identity of the unknown sample.

Following instruction sequence 78, the program enters decision sequence 79 which the operator is asked if he wishes to test another unknown sample. If the operator answers "yes" in decision sequence 79, the program returns to routine 73 and the process repeats for the next unknown sample. If the answer is "no" in instruction sequence 79, the program terminates.

The Fortran listing in the appendix is also operable to carry out program illustrated in FIG. 3.

Figure 4:
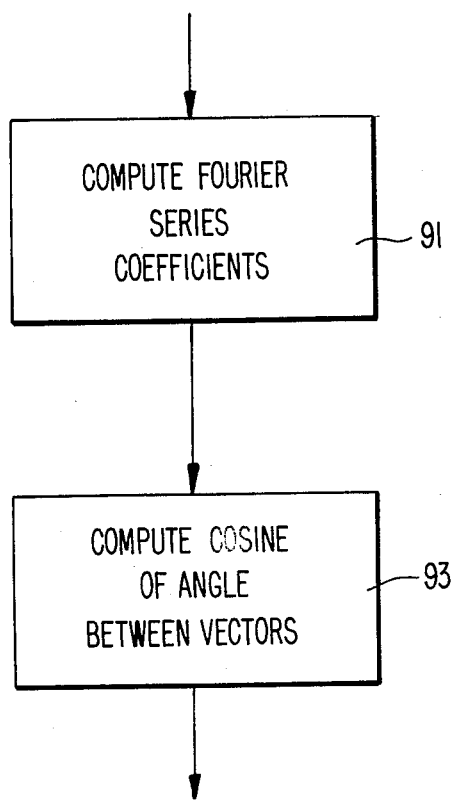
FIG. 4 is a flowchart of an alternative set of routines to be used in either the method of FIG. 2 or the method of FIG. 3.

In each of the embodiments described above, the derivative curves are represented as vectors by having each of the values of the amplitude of the curve at incrementally spaced index points along the curve represent the coordinates of the end point of a vector. An alternative method of comparing the spectral derivative curves, illustrated in FIG. 4, is carried out by computing a Fourier series in routine 91 to represent each derivative curve from the set of values representing the derivative curve by amplitude sample. The Fourier series computation will result in the determination of a plurality of coefficient values, one for each frequency term of the Fourier series. In this manner, a set of values will accurately represent the derivative with a substantially smaller number of values than a set of values which represent the derivative by its amplitude at incrementally spaced index points. For example, the derivative curve can be accurately represented by 20 frequency terms as opposed to 700 amplitudes at incrementally spaced index points. Following routine 91, in routine 93, the coefficients of the frequency terms of each Fourier series are assumed to represent the coordinates of an end point of a vector, one for each Fourier series. The cosine between the vectors is computed in the same manner as described above to determine an index of the similarity between samples.

When the alternative method of comparing derivative spectral curves is used for determining whether a test material matches a standard material, the program of FIG. 2 is followed except that routines 91 and 93 of FIG. 4 are substituted in place of routine 39 and in place of routine 56. When the alternative method of comparing derivative spectral curves is employed to identify an unknown material, the program of FIG. 3 is followed except that the data inputted into the computer in instruction sequence 71 will be the coefficients of the Fourier series for the derivative reflectivity curves in the near infrared spectrum for each of the different materials to be matched against the unknown sample. Also, the routines 91 and 93 illustrated in FIG. 4, are substituted for routine 76. When this Fourier series alternative method is employed for the method of FIG. 3, data representing a larger number of known materials may be inputted and stored in the computer since each derivative spectral reflectivity curve for each material can be accurately represented by a relatively small number of values.

The Fortran listing in the appendix includes the option of matching the spectra by Fourier series illustrated in FIG. 4.

The above description is of preferred embodiments of the invention and modifications may be made thereto without departing from the spirit and scope of the invention, which is described in the appended claims.

What is claimed is:

1. A method of determining whether the composition of a test material is the same as the composition of a standard material, said test material and said standard material each having a reflectivity, comprising the steps of measuring the reflectivity of the standard material throughout a range of the near infrared spectrum to produce a measurement of reflectivity, determining from the measurement of the reflectivity of the standard material a first set of n values representing a derivative of any variation of reflectivity with wavelength throughout said range, measuring the reflectivity of said test material throughout said range to produce a measurement of reflectivity, determining from the measurement of the reflectivity of said test material a second set of n values representing a derivative of any variation of the reflectivity of said test material with wavelength throughout said range, defining a first vector having an end point in n-dimensional space represented mathematically by said first set of n values as coordinates of the end point of said first vector, defining a second vector having an end point in n-dimensional space represented mathematically by said second set of n values as the coordinates of the end point of said second vector, and determining the cosine of any angle between first and second vectors as an index of similarity of the composition of said test material and the composition of said standard material.

2. A method as recited in claim 1, wherein said first and second vectors have magnitudes, and wherein said cosine is determined by determining the vector dot product of said first vector and said second vector divided by the product resulting from multiplying the magnitudes of said first and second vectors.

3. A method as recited in claim 1, wherein said first set of values consists of amplitudes of the derivative determined from the measurement of the reflectivity of said standard material at spaced index points throughout said range and wherein said second set of values consists of amplitudes of the derivative determined from the measurement of the reflectivity of said test material at said spaced index points throughout said range.

4. A method as recited in claim 1, wherein said first set of values are coefficients of terms of a Fourier series representing the derivative determined from the measurement of the reflectivity of said standard material and wherein said second set of values are coefficients of terms of a Fourier series representing the derivative determined from the reflectivity measurement of said test material.

5. A method as recited in claim 1, wherein said steps of measuring reflectivity of the test material, determining a second set of values, defining a second vector, and determining the cosine are performed on each of a plurality of batches of test material to determine a plurality of cosine values, one for each of said batches and segregating the batches for which the cosine value determined is less than a predetermined minimum value from the batches of material for which the cosine value determined is equal to or greater than said predetermined minimum value.

6. A method as recited in claim 5, wherein said predetermined minimum value is determined by measuring the reflectivity of said standard material in said range a plurality of times, determining a plurality of sets of n values each representing a derivative of the variation of reflectivity of said standard material throughout said range measured by a different one of said plurality of measurements, said first set of values being average values determined from said plurality of measurements, defining a vector in n-dimensional space represented mathematically by each set of values of said plurality of sets of n values as the coordinates of the end point of such vector whereby a plurality of vectors are defined corresponding to said plurality of measurements, determining the cosine between each vector of said plurality of vectors and said first vector to provide a plurality of cosine values and selecting the smallest value of said plurality of cosine values as said predetermined minimum value.

7. A method of identifying the composition of an unknown material comprising storing a multiplicity of sets of values each determined from and corresponding to a different one of a multiplicity of materials of different compositions, one of which is the same composition as the composition of said unknown material, each set of values representing a derivative of any variation in reflectivity with wavelength of the corresponding one of said multiplicity of materials throughout a range in the near infrared spectrum, measuring the reflectivity of said unknown material througout said range, determining a further set of values from the measurement of the reflectivity of said unknown material, said further set of values representing a derivative of any variation in the reflectivity of said unknown materiall with wavelength throughout said range, defining a vector having an end point for each set of values of said multiplicity and represented mathematically by such set of values as coordinates of the end point of such vector in multidimensional space, thereby defining a multiplicity of vectors, one for each of said multiplicity of materials, defining a further vector having an end point and represented mathematically by the values of said further set of values as coordinates of the end point of said further vector in multidimensional space, determining the cosine of any angle between said further vector and each vector of said multiplicity of vectors to thereby determine a multiplicity of cosine values, one for each of said multiplicity of materials and identifying the composition of said unknown material as the same as that for which a highest cosine value is determined in said step of determining the cosine of the angle between said further vector and each vector of said multiplicity of vectors.

8. A method as recited in claim 7, wherein said vectors have magnitudes and said cosines are determined by determining the vector dot product of said further vector and each vector of said multiplicity of vectors divided by the product resulting from multiplying the magnitudes of said further vector and such vector of said multiplicity of vectors.

9. A method as recited in claim 7, wherein said multiplicity of sets of values consist of amplitudes of the derivatives corresponding to said multiplicity of materials sampled at spaced index points throughout said range and wherein said further set of values consists of amplitudes of the derivatives determined from the measurement of the reflectivity of said unknown material at said spaced index points throughout said range.

10. A method as recited in claim 7, wherein said multiplicity of sets of values consist of coefficients of terms of a Fourier series representing the derivatives corresponding to said multiplicity of materials and wherein said further sets of values consist of coefficients of terms of a Fourier series representing the derivative determined from the reflectivity measurement of said unknown material.

* * * * *